United States Patent
Schaller et al.

(10) Patent No.: US 10,765,385 B1
(45) Date of Patent: Sep. 8, 2020

(54) POSITIONING APPARATUS FOR VETERINARY DENTAL FILM AND DIGITAL SENSORS

(71) Applicants: Bret Schaller, Sanford, NC (US);
Diane K Schaller, Sanford, NC (US)

(72) Inventors: Bret Schaller, Sanford, NC (US);
Diane K Schaller, Sanford, NC (US)

(*) Notice: Subject to any disclaimer, the term of this patent is extended or adjusted under 35 U.S.C. 154(b) by 534 days.

(21) Appl. No.: 15/151,492

(22) Filed: May 11, 2016

(51) Int. Cl.
*A61B 6/00* (2006.01)
*A61B 6/14* (2006.01)

(52) U.S. Cl.
CPC ............ *A61B 6/4405* (2013.01); *A61B 6/145* (2013.01); *A61B 6/508* (2013.01)

(58) Field of Classification Search
CPC ................................ A61B 6/145; A61B 6/508
See application file for complete search history.

(56) References Cited

U.S. PATENT DOCUMENTS

2005/0013413 A1* 1/2005 Cochran ............... A61B 6/145
378/205

* cited by examiner

*Primary Examiner* — Dani Fox

(57) ABSTRACT

A dental radiographic positioner and film holder assembly has a film plane reference component (2) configured to detachably affix to a shaft (1a) extending from the edge of the film holder (1). Affixing surfaces (1b, 2b) are provided between the shaft (1a) and film plane (2) to enable longitudinal movement and restrict rotational movement. A teeth plane reference component (3) is detachably affixed to the shaft (1a). A bisecting angle reference component (4) is detachably affixed to the shaft (1a). Both the bisecting angle plane (4) and teeth plane (3) are attached to allow for longitudinal motion along the shaft (1a) as well as rotational motion around the axis of the shaft (1a).

22 Claims, 11 Drawing Sheets

POSITIONING APPARATUS FOR VETERINARY DENTAL FILM AND DIGITAL SENSORS

CROSS-REFERENCES TO RELATED APPLICATIONS

There are no provisional or earlier dated applications related to this matter.

STATEMENT REGARDING FEDERALLY SPONSORED RESEARCH OR DEVELOPMENT

There are no federal or other sponsors related to this matter.

THE NAMES OF THE PARTIES TO A JOINT RESEARCH AGREEMENT

This matter is not the product of a joint research agreement.

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Compact discs labeled Copy 1 and Copy 2 are included in this submission. These discs do not contain new material or subject matter relating to this application. These discs have been provided solely for the purpose of expediting the USPTO in the conversion of this paper submission into digital media for inclusion in the patent database. All sections included are labeled as such in portable document format on both discs.

STATEMENT REGARDING PRIOR DISCLOSURES BY THE INVENTOR OR A JOINT INVENTOR

There have been no disclosures made outside of filing the patent.

BACKGROUND OF THE INVENTION

Technical Field of the Invention

The present invention is a radiographic film or sensor holder apparatus having a sensor mount and aiming ring mounted to an extension arm, for use during veterinary dental radiographic procedures. More particularly, the invention is a modular sensor holder assembly having a sensor mount, tooth plane reference, sensor plane reference, and an aiming ring reference. The aiming ring reference depicts the bisecting angle ideally suited for accurate radiographs. Movement of the aiming ring reference longitudinally along the support arm facilitates a plurality of patient oral cavity sizes and lengths to be accommodated. Different sensor mount options facilitate a plurality of digital and film type radiograph media to be used.

Background Art

Dental radiographs are made by projecting x-rays collimated with a cone or tube head through the teeth onto a dental film. The x-ray apparatus is configured with a movable tube head capable of proximate placement to the patient's oral cavity. Dental films and digital film sensors are available in a variety of rectangular sizes all with a thin cross section. The flat rectangular surface reduces distortion of the images being captured. The small thin shape facilitates placement inside the oral cavity.

In the veterinary industry, many different species are treated. These patients are commonly under general anesthesia during these procedures. A need exists therefore, for a film holder assembly that does not require the patient to bite onto the apparatus to hold it in position. General anesthesia prevents this level of cooperation from the patient. Additionally, there are many characteristics unique to each species in mandible shape and size, teeth shape and size, teeth number, teeth occlusion and upper and lower palette configuration. Within the canine species alone there exists significant variation in the dental arcade across all the various canine breeds. With these differences, a need exists for an apparatus that would provide a visual reference plane to align the x-ray tube head for proper film exposure. When working with the human species, an example of a film holder with a bite block is found in Pat. No. US20110051900 A1.

Dental radiographic images are captured using two well known techniques, the parallel and the bisecting angle. These same techniques are used in the human species as thoroughly described by Updegrave in U.S. Pat. No. 3,473,026. When a veterinary patient is under general anesthesia the film orientation is not held in place by use of a bite block. The film, once inserted into the oral cavity behind the teeth often moves from the desired position. This movement often goes undetected until after the radiographic image has been processed. Improper orientation results in distorted and or out of focus images. Additionally, improper orientation or alignment may result in the desired subject matter of the radiograph being entirely missing from the resulting captured image. These iterations of missed or unusable radiographs subject the patients to unnecessary radiation exposures.

A need exists therefore, for a sensor or film holder that when positioned proximate to the teeth, will indicate sensor orientation and placement to the operator outside the oral cavity. It has also been found that a need exists for a holder that provides a visual indication of the sensor orientation relative to the teeth plane and bisecting angle. Displaying these orientations, simultaneously to the operator significantly improves their ability to capture images and eliminate distortions, improper focus, and repeated radiation exposures to the patient for images unsuitable for diagnostic purposes.

BRIEF SUMMARY OF THE INVENTION

It is an object of the invention to provide a holder for dental film, a digital film sensor, or any similar device intended to capture x-rays in the production of veterinary dental radiographic images.

It is a further object of the invention to provide a slender support structure connected to the film holder allowing for placement of the holder into the oral cavity of a canine, feline, or other species commonly serviced by small animal, large animal, and exotic species veterinarians.

It is yet another object of the invention that the support structure be sufficiently long to hold the film in position for the caudal maxillary and mandibular arcade and still protrude out of the oral cavity It is yet another object of the invention that the support structure hold the various components necessary to represent the teeth, sensor, and bisecting angle planes.

It is yet another object of the invention that the reference planes are movable to allow for alignment with the planes defined by the teeth and the bisecting angle.

In general, the position apparatus is comprised of a film holder at one end of a support arm with the movable reference planes at the other end. Translational movement along the support arm is possible to maintain close proximity of the reference planes to the film sensor.

Numerous embodiments of the subject position apparatus are shown in the accompanying drawings.

DETAILED DESCRIPTION OF THE INVENTION

Preferred Embodiments for Carrying Out the Invention

An x-ray film or digital film sensor holder is designated by the number 1 on the attached drawings. As depicted it is rectangular however this size and shape could be any that is necessary to fit the variety of films and sensors available in the industry.

Figure 10:
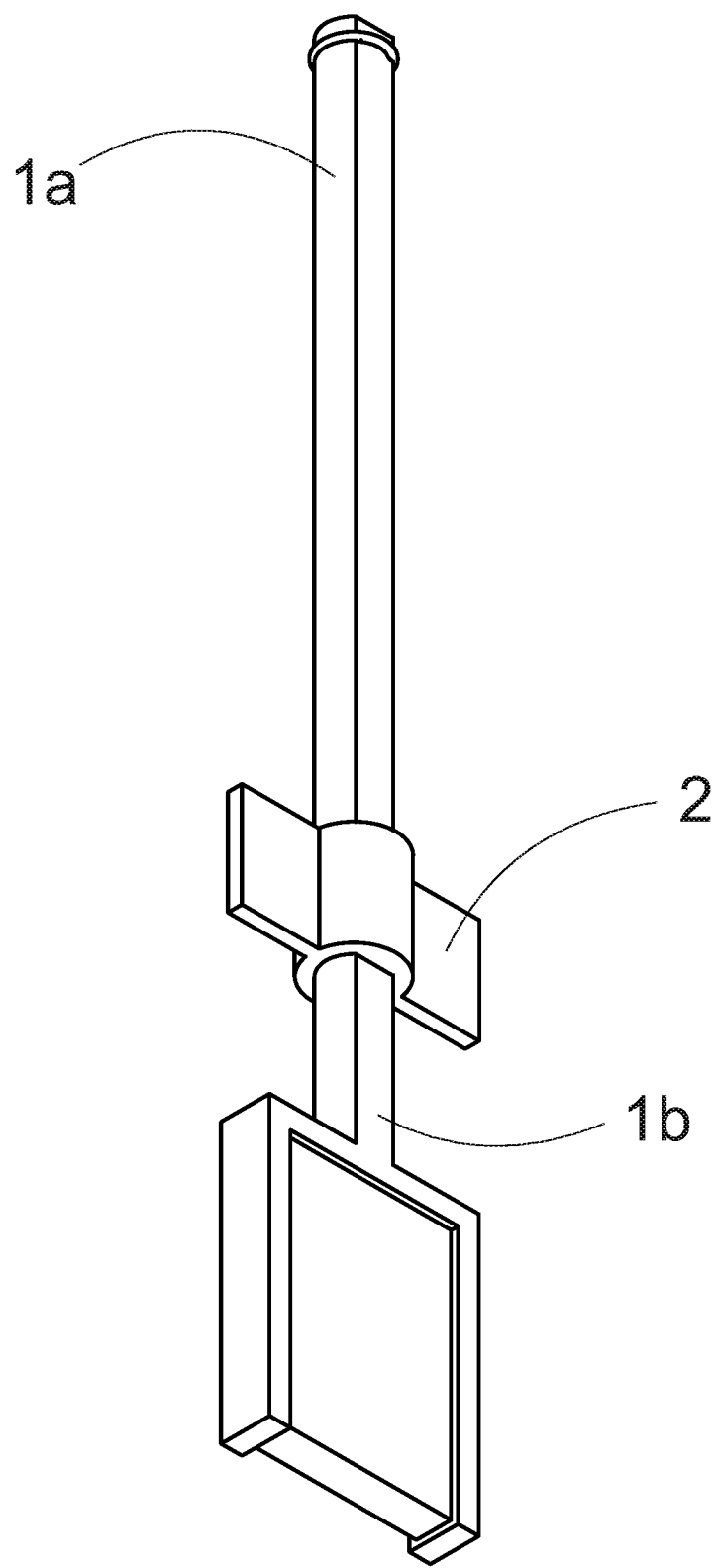
FIG. 10 is a perspective view of the dental radiographic positioner and film holder assembly with only the film plane, film holder, and film sensor shown.
Figure 11:
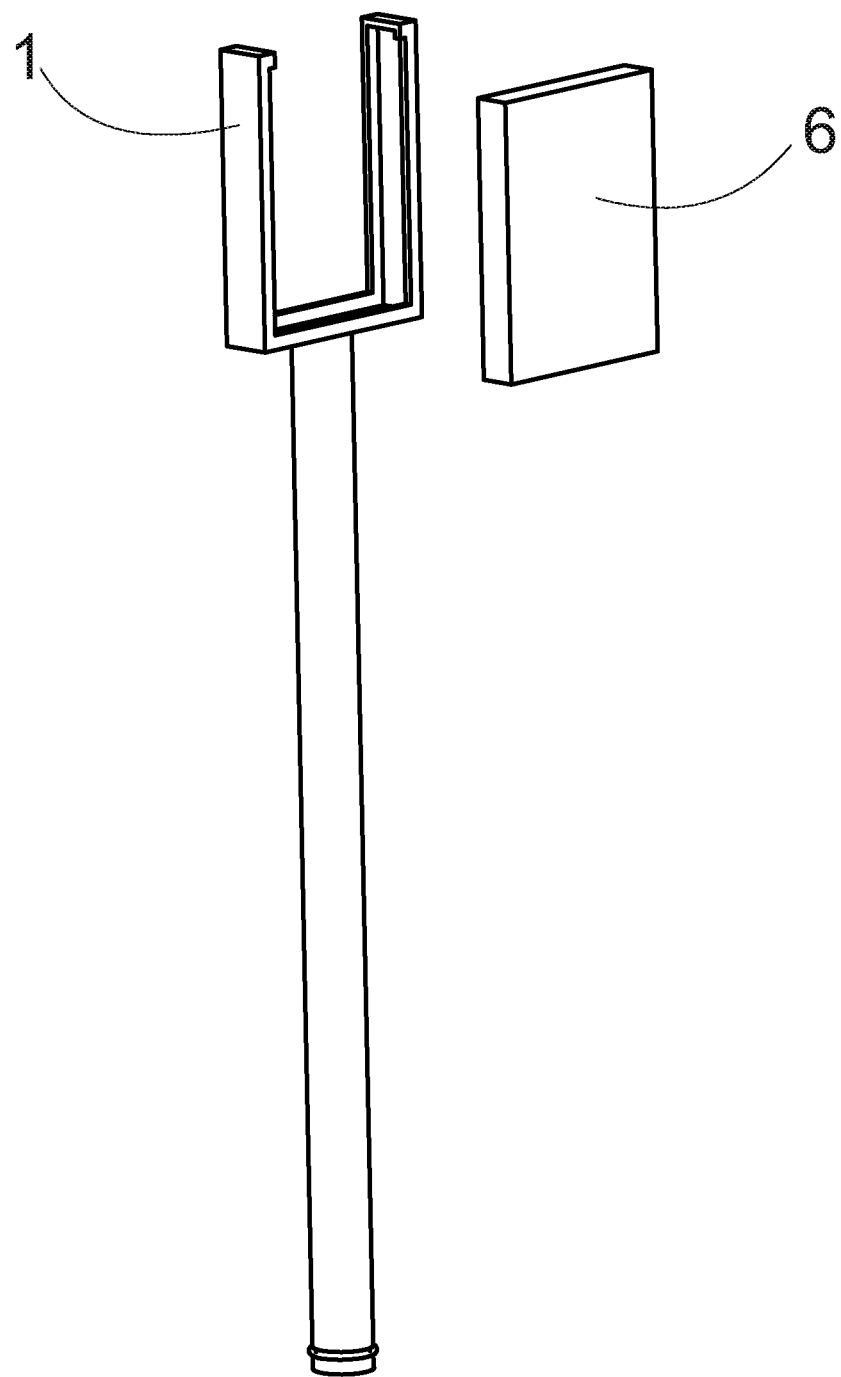
FIG. 11 is a perspective, exploded view of the film holder and dental film sensor.

The film plane reference is designated by the number 2 on the attached drawings. Having obstructed or no visibility of the film orientation inside the oral cavity, the film plane reference component provides the visual plane of reference outside the mouth. This reference plane is held parallel to the film plane along the full length of the shaft 1a. Allowing a degree of freedom for movement along the film holder shaft 1a, yet restricting the degree of freedom for rotation about the shaft can be accomplished by many different methods. FIG. 10 illustrates a flat surface on the film holder shaft 1b mated to a flat surface breaking the cylindrical mating surface inside the film plane reference 2. This may also be accomplished with many different approaches depending on the materials used or manufacturing methods employed to create the embodiment. For instance two mating splined surfaces or a key groove along the shaft could just as easily be used. Any attachment means between the film holder shaft 1a and the film plane reference 2 that maintains the aforementioned degrees of freedom is within the scope of the invention.

When anesthetizing patients for medical treatments it is generally preferred to minimize the duration of anesthesia to the shortest possible time necessary to complete the desired medical procedures. The placement of the film plane reference 2 adjacent to the teeth plane reference 3 inside the bisecting angle plane reference 4 is intentional to allow for rapid identification of the desired x-ray tube head position. Additionally, features for improving the manual positioning of the teeth and bisecting angle references have been provided as 3a and 4a. Any style of knurled, smooth, tabbed grip or wheel type feature is within the scope of the present invention.

As depicted, the teeth reference 3 and bisecting angle reference 4 do not have angular indicators of their position. The invention as shown allows for positioning the components relative to the patient with the accuracy of the human eye. The addition of laser lights embedded on the film holder projecting out of the oral cavity onto a surface or simply providing a beam to be 'broken' when the bisecting angle has been properly aligned is also within the scope of this invention. Additionally the incorporation of radial position sensors on the film holder shaft 1a to provide positioning cues either audible or visual for the teeth 3 and bisecting angle 4 references is also within the scope of this invention.

Figure 1:
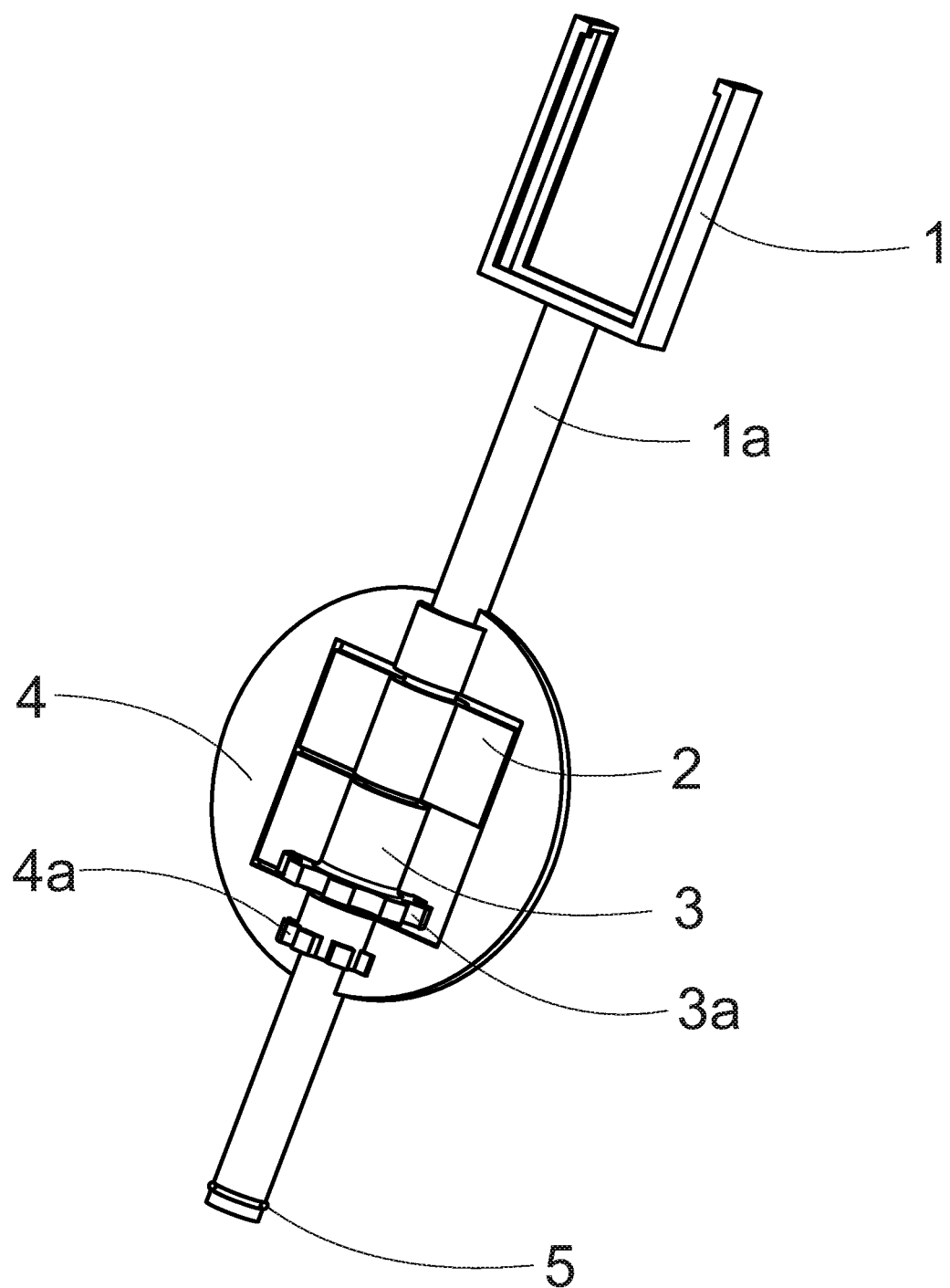
FIG. 1 is a perspective view of the dental radiographic positioner and film holder assembly, embodying the concepts of the present invention.
Figure 2:
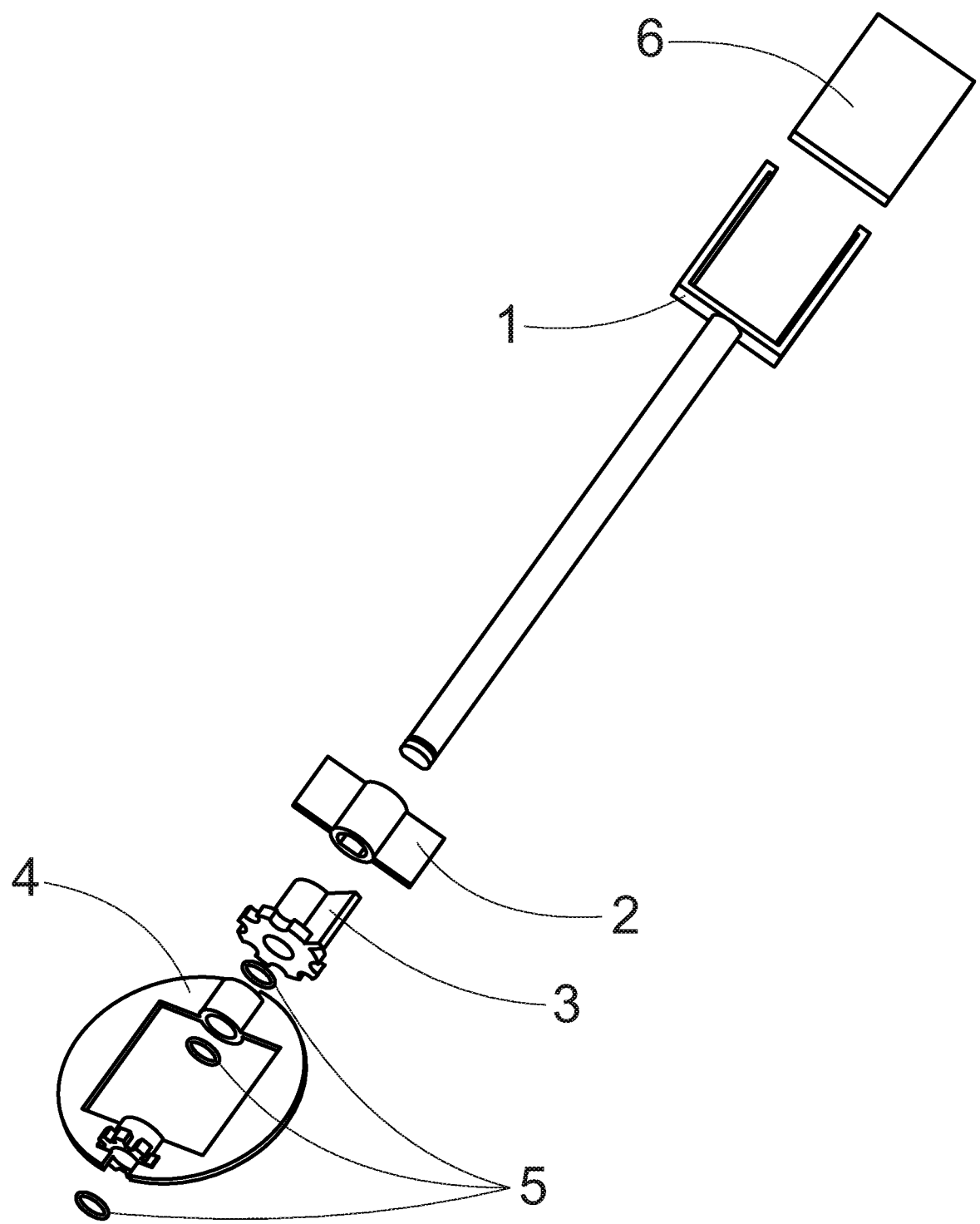
FIG. 2 is a perspective, exploded view of the dental radiographic positioner and film holder assembly, embodying the concepts of the present invention.
Figures 3, 4:
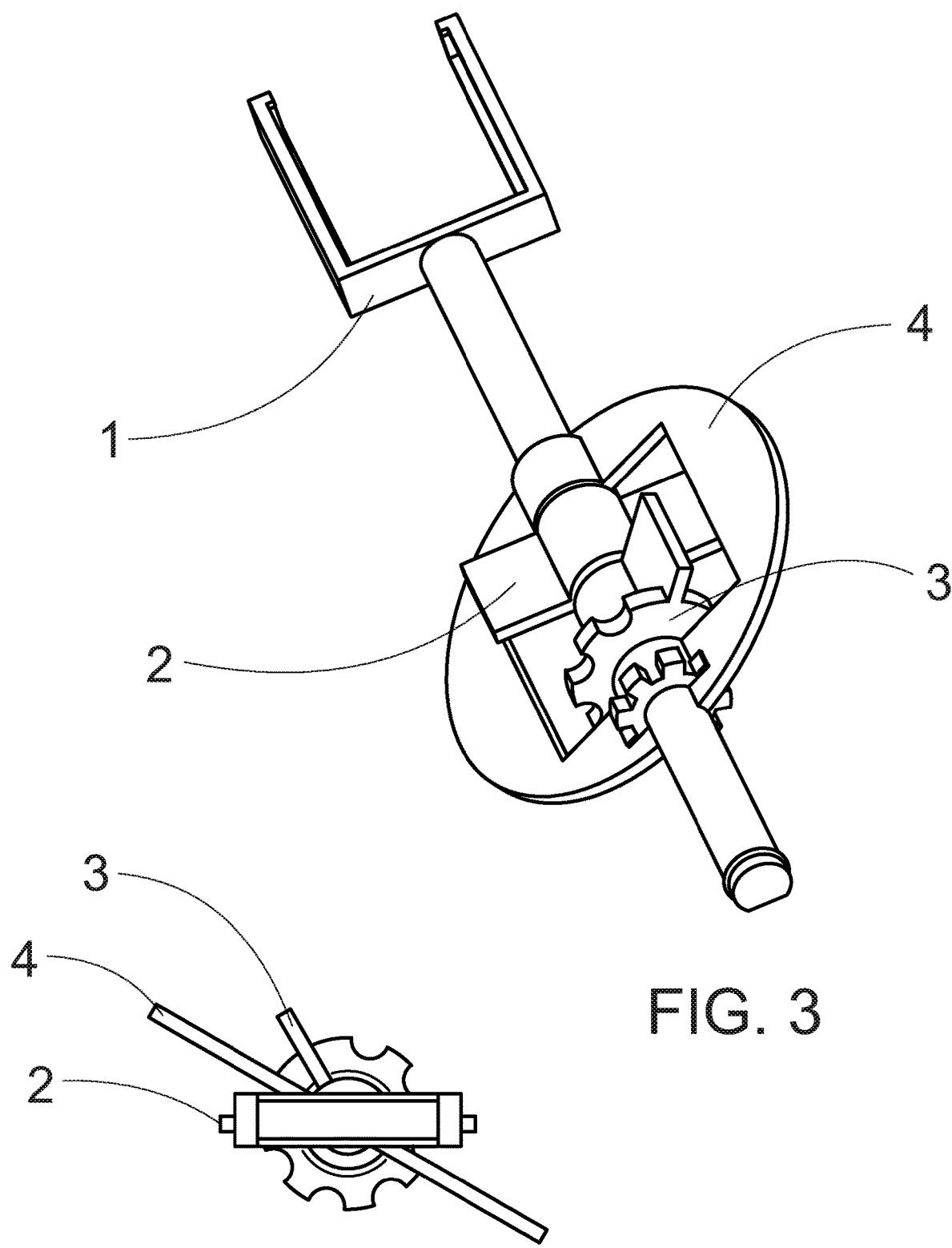
FIG. 3 is a perspective view of the dental radiographic positioner and film holder assembly, showing alternate positions of the bisecting angle plane and teeth plane, embodying the concepts of the present invention.
FIG. 4 is an end view of FIG. 3.
Figure 5:
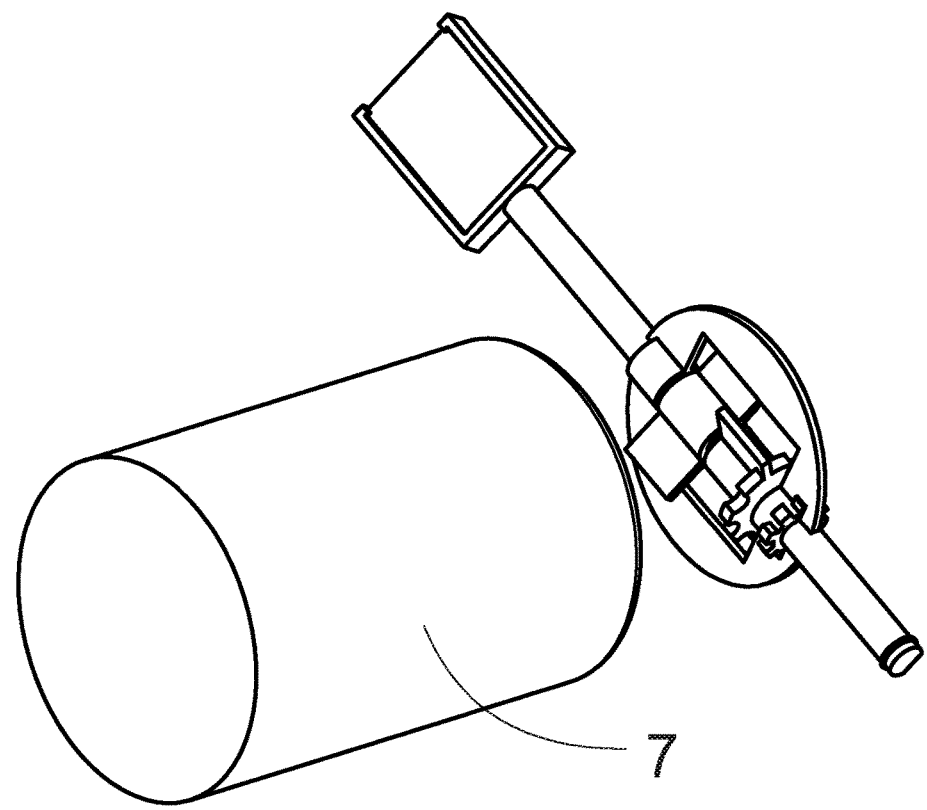
FIG. 5 is a perspective view of the dental radiographic positioner and film holder assembly including the x-ray tube head positioned over the bisecting angle plane.
Figure 6:
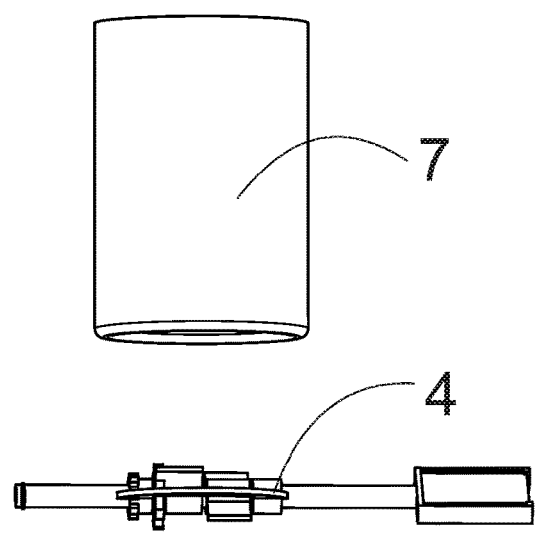
FIG. 6 is a top view of FIG. 5.
Figure 7:
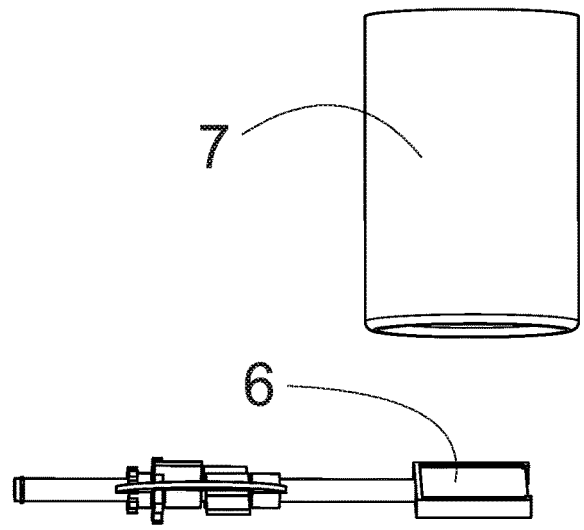
FIG. 7 is a top view of FIG. 5 with the x-ray tube head repositioned over the dental film holder.
Figures 8, 9:
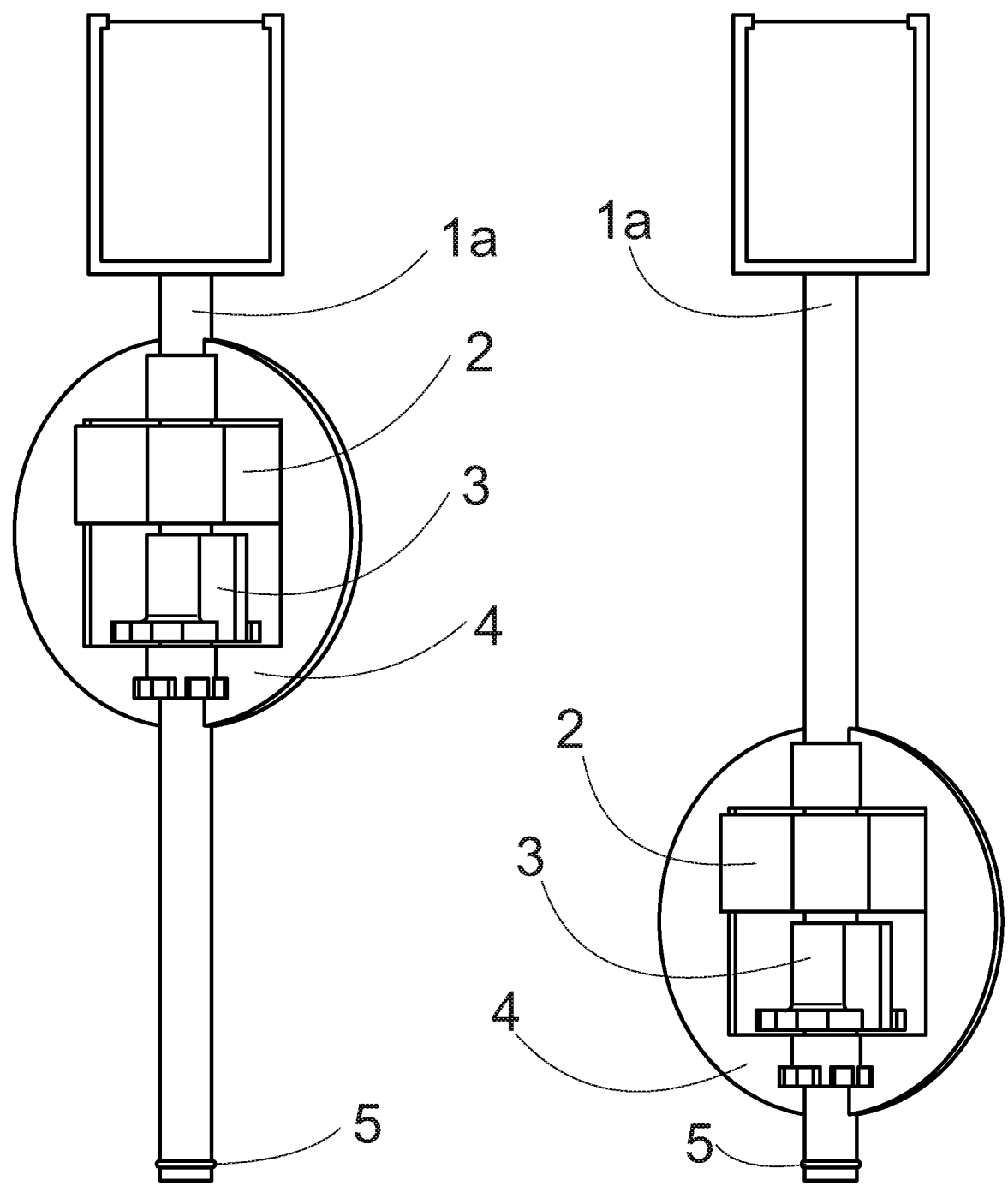
FIG. 8 is a top view of the dental radiographic positioner and film holder assembly with the reference plane components all positioned closely to the film holder.
FIG. 9 is a top view of the dental radiographic positioner and film holder assembly with the reference plane components all positioned away from the film holder assembly.

The teeth plane reference 3 and bisecting angle plane reference 4 require both the ability to rotate about the film holder shaft 1a for positioning of the x-ray tube head 7 and the ability to stay in position when the radiograph is captured. This complex joint between these components has been demonstrated with the use of o-rings 5 as shown in the exploded view FIG. 2. Friction created by a controlled interference fit between the mating profiles could also be employed. Similarly a ball bearing, glide bearing, bushing or other means of controlling the friction between two moving components would be within the scope of this invention.

Another preferred embodiment includes gears between the moving components. The use of gears could enable the movement and static requirements of the components. Additionally gears could be employed to drive for instance the bisecting angle plane reference 4 into position as the teeth plane reference 3 is aligned with the patient's teeth.

In addition to maintaining the level of friction between the moving components, the o-ring 5 is also used as a stop or restriction preventing the operator from unintentionally disassembling the apparatus when adjusting the reference planes to the end of the film holder shaft 1a. This function could easily be achieved any number of different ways for instance with an e-clip, snap ring, even a diameter change or step in the film holder shaft 1a.

Figure 12:
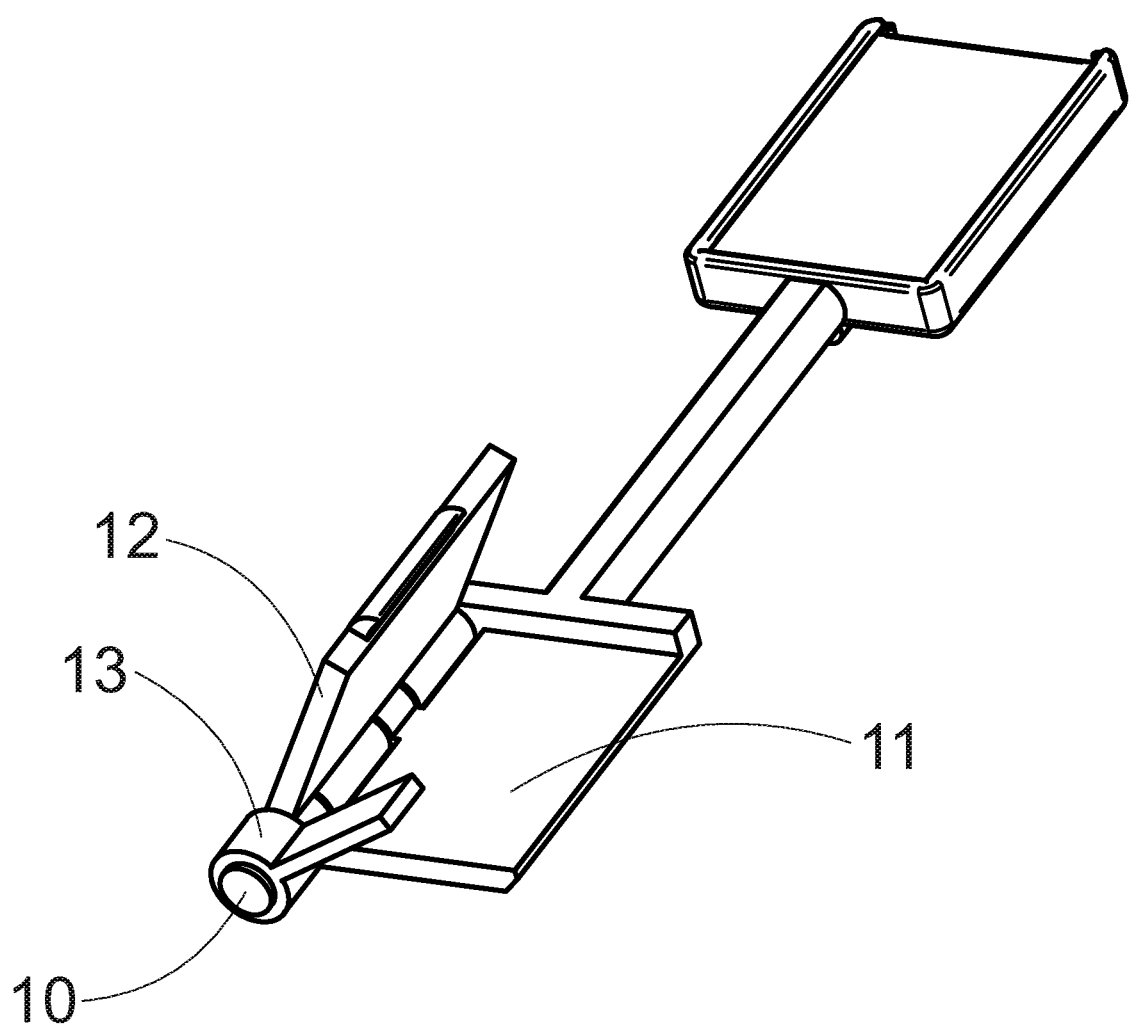
FIG. 12 is an alternative embodiment of the radiographic positioner and film holder assembly according to the invention.

An alternative embodiment depicted in FIG. 12 moves the axis of rotation for the bisecting angle indicator 13 and the teeth plane reference 12 out of alignment with the film holder shaft 1a. This provides larger distances between the edges of teeth angle reference 3 and the film plane reference 2 for the same degree of rotation in the previous embodiment.

Figure 13:
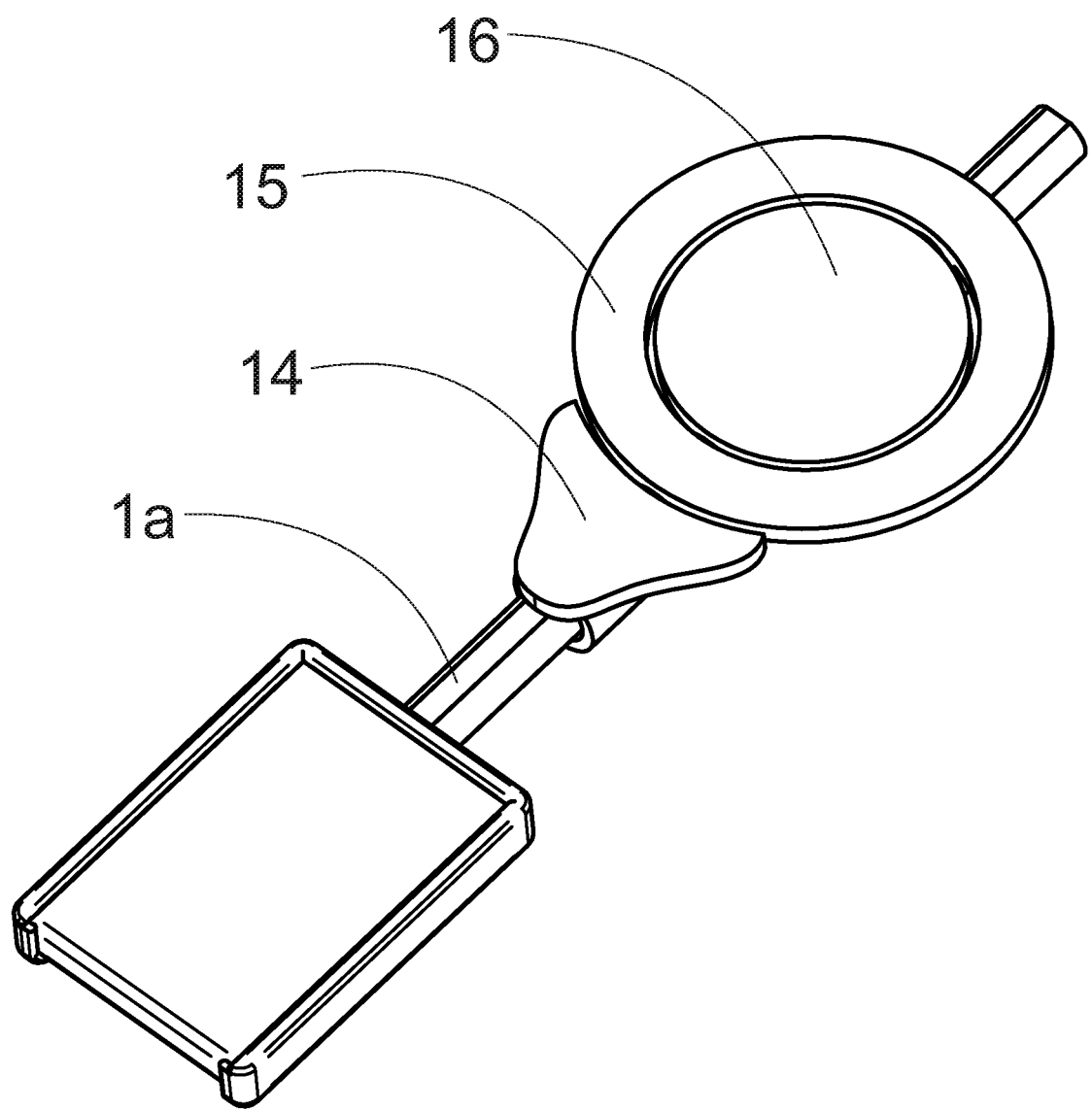
FIG. 13 is an alternative embodiment of the radiographic positioner and film holder assembly, according to the invention.

An alternative embodiment depicted in FIG. 13 moves the film plane reference 14 outside the circle of the bisecting angle plane reference 16. This provides a larger teeth plane reference 15. This embodiment is not limited to the physical shapes shown in FIG. 13.

Figure 14:
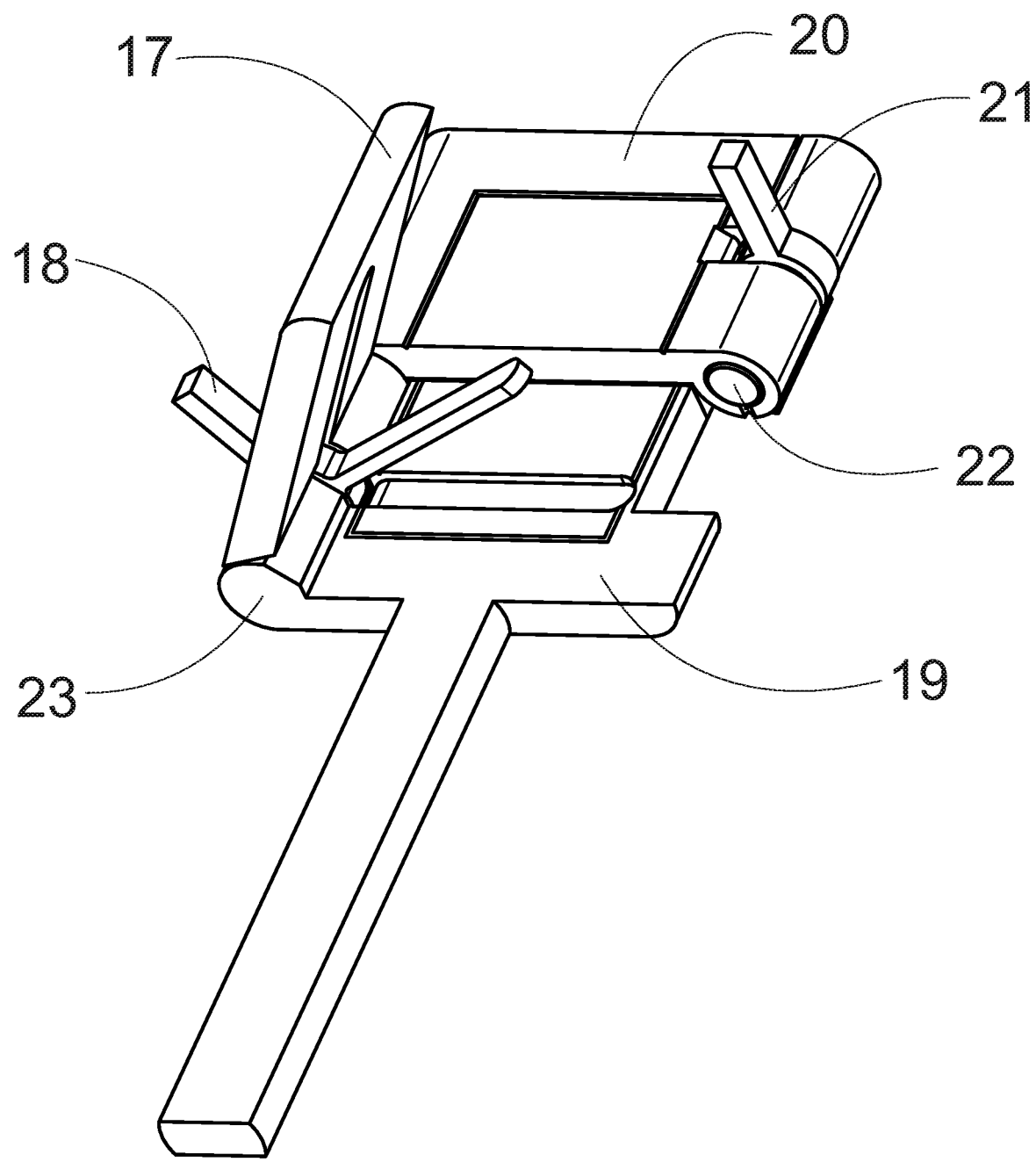
FIG. 14 is an alternative embodiment of the radiographic positioner and film holder assembly, according to the invention.

An alternative embodiment depicted in FIG. 14 provides two opposing offset axes of rotation 22 and 23 equidistant from the film holder shaft major axis 1a. The teeth plane references 17 and 20 along with the bisecting angle indicators 18 and 21 are also provided in opposing or mirrored configurations. Providing opposing sets of reference planes allows for a closer approximation of the actual teeth and film as positioned in either the upper right jaw and lower left mandible versus the upper left jaw and lower right mandible. The film holder is not shown in FIG. 14.

Figure 15:
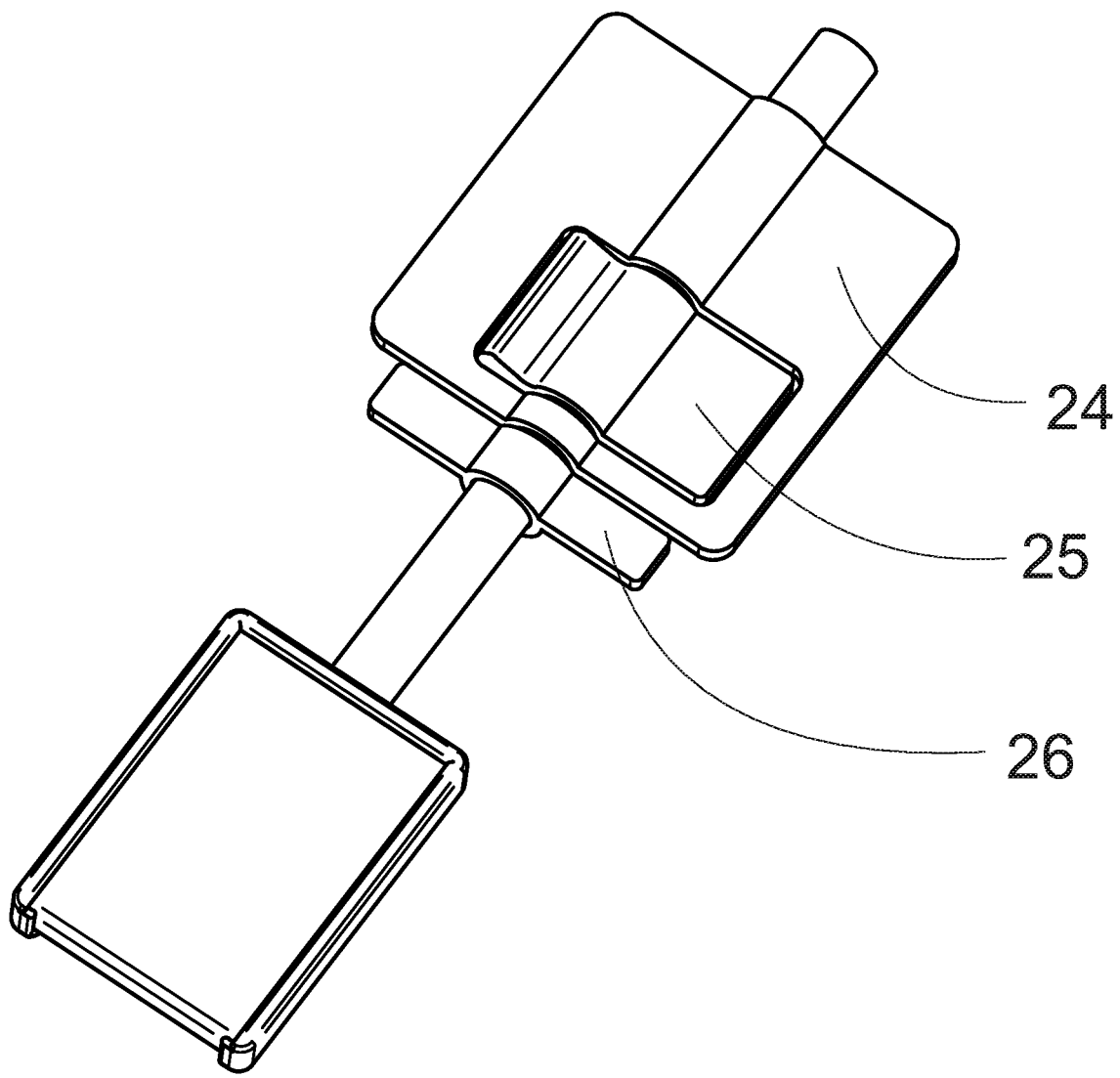
FIG. 15 is an alternative embodiment of the radiographic positioner and film holder assembly, according to the invention.

An alternative embodiment depicted in FIG. 15 shares the film plane reference 26 outside the bisecting angle plane reference 24 similar to FIG. 13. This embodiment increases the surface area of either the tooth plane reference 25 or the bisecting angle plane reference 24 or both.

What is claimed is:

1. An apparatus for determining the bisecting angle plane of reference in veterinary dentistry comprising:
    a film or digital sensor holder having a support arm,
    a component having a planar surface that remains parallel to the film exposure plane, and two independent components having planar surfaces that freely rotate about the support arm;
    wherein the film holder exterior shape depicts a rectangular prism affixed to a shaft aligned such that the major axis of the shaft is colinear with the major axis of the film holder;
    wherein the film holder is made up of a semirigid material with elastic properties that allow for small deformations for fitment of a variety of film or digital sensors;
    wherein the plurality of planar surface components are detachably affixed to the support arm by means of interfacing surfaces that allow for longitudinal movement along the support arm major axis;
    wherein the planar surface parallel to the film sensor is fixed from rotational motion about the shaft axis by means of splines, keys, or other non circular geometric interfacing surfaces between the two components;
    wherein two rotating reference planes are detachably affixed to the support arm allowing both longitudinal and rotational motion along and around the support arm major axis.

2. The invention of claim 1, wherein the film holder is comprised of multiple components movably affixed together that allow for adjustment to fit a variety of film or digital sensor sizes.

3. The invention of claim 1, wherein the film holder shaft is comprised of an inner and outer component nested together to allow for telescoping movement to vary the overall length of the film holder assembly.

4. The invention of claim 1, wherein the film holder shaft has an affixed component at the end opposite the film holder to retain the various reference plane components assembled onto the shaft.

5. The invention of claim 1, wherein the film holder shaft has the plurality of components to visually represent the film reference plane, the tooth reference plane and the bisecting angle reference plane for purposes of capturing a radiographic image.

6. A film reference plane as in claim 5, wherein the perimeter of the planform view of the component describes a plane.

7. A film reference plane as in claim 5, wherein the plane of the component remains parallel to the plane of the film.

8. A film reference plane as in claim 5, wherein the perimeter when viewed from the edge is sufficiently thin as to provide an unaided visual cue to the position of the plane relative to the adjoining tooth and bisecting angle reference planes.

9. A tooth reference plane as in claim 5, wherein the perimeter of the planform view of the component describes a plane.

10. A tooth reference plane as in claim 5, wherein an axis of rotation through the plane allows the reference surface to be positioned at any place in the 360 degrees of rotation about the film holder support arm.

11. A tooth reference plane as in claim 5, wherein a knurled, textured, or otherwise defined grip allows the operator to easily position the reference plane.

12. A tooth reference plane as in claim 5, wherein the perimeter when viewed from the edge is sufficiently thin as to provide an unaided visual cue to the position of the plane relative to the adjoining film and bisecting angle reference planes.

13. A tooth reference plane as in claim 5, wherein an internal bearing surface enables movement of the reference plane when desired, yet still has sufficient friction to remain motionless when not being purposefully moved.

14. A bearing surface as in claim 13, wherein the film support arm interface with the tooth reference plane is manufactured with dimensional clearances sufficient to achieve the forced movement and static positioning as described.

15. A bearing surface as in claim 13, wherein the use of impregnated polymer inserts or parent components is sufficient to achieve the forced movement and static position as described.

16. A bearing interface as in claim 13, wherein a bearing of ball bearing, roller bearing, glide bearing, or lubricated material such as an o-ring construction is employed to achieve the forced movement and static position as described.

17. A bisecting angle reference plane as in claim 5, wherein the perimeter of the planform view of the component describes a plane.

18. A bisecting angle reference plane as in claim 5, wherein an axis of rotation through the plane allows the reference surface to be positioned at any place in the 360 degrees of rotation about the film holder support arm.

19. A bisecting angle reference plane as in claim 5, wherein the tooth and film reference planes either fit inside or can be positioned immediately adjacent to the outer edges along the film holder support arm axis.

20. A bisecting angle reference plane as in claim 5, wherein the perimeter when viewed from the edge is sufficiently thin as to provide an unaided visual cue to the position of the plane relative to the adjoining film and tooth reference planes.

21. A bisecting angle reference plane as in claim 5, wherein a knurled, textured, or otherwise defined grip allows the operator to easily position the reference plane.

22. A bisecting angle reference plane as in claim 5, wherein the interfacing surfaces with the film holder support arm contain the same movable relationship and bearing configuration options as claimed in claim 13, claim 14, claim 15, and claim 16.

* * * * *